United States Patent [19]

Tuttle

[11] 4,424,209

[45] Jan. 3, 1984

[54] 3,4-DI-ISOBUTYRYLOXY-N-[3-(4-ISOBUTYRYLOXYPHENYL)-1-METHYL-N-PROPYL]-BETA-PHENETHYLAMINE CYCLODEXTRIN COMPLEXES

[75] Inventor: Ronald R. Tuttle, Plantation, Fla.

[73] Assignee: Key Pharmaceuticals, Inc., Miami, Fla.

[21] Appl. No.: 390,349

[22] Filed: Jun. 21, 1982

[51] Int. Cl.³ .................... A61K 31/73; C08B 37/16
[52] U.S. Cl. ..................................... 424/180; 536/46
[58] Field of Search ........................... 536/46; 424/180

[56] References Cited

U.S. PATENT DOCUMENTS 3,987,200  10/1976  Tuttle et al. .................... 424/330
4,228,160  10/1980  Szejtli et al. .................... 424/180

*Primary Examiner*—Johnnie R. Brown
*Assistant Examiner*—Elli Peseler
*Attorney, Agent, or Firm*—Wegner & Bretschneider

[57] ABSTRACT

Cardiac contractility agents are provided which are 3,4-di-isobutyryloxy-N-[3-(4-isobutyryloxyphenyl)-1-methyl-n-propyl]-beta-phenethylamine, preferably orally deliverable forms which are cyclodextrin complexes.

4 Claims, No Drawings

3,4-DI-ISOBUTYRYLOXY-N-[3-(4-ISOBUTYRYLOXYPHENYL)-1-METHYL-N-PROPYL]-BETA-PHENETHYLAMINE CYCLODEXTRIN COMPLEXES

BACKGROUND OF THE INVENTION

The present invention relates to improved oral cardiac contractility agents, including compounds based upon 3,4-dihydroxy-N-[3-(4-hydroxyphenyl)-1-methyl-n-propyl]-beta-phenethylamine, disclosed in Tuttle et al, U.S. Pat. No. 3,987,200. Other improvements over Tuttle et al are found in my copending application Ser. No. 381,567, filed May 24, 1982 entitled "Oral Cardiac Contractility Agent", which discloses a cyclodextrin complex of 3,4-dihydroxy-N-[3-(4-hydroxyphenyl)-1-methyl-n-propyl]-beta-phenethylamine.

Selective 0-acylations of compounds containing amino and phenolic groups may be performed by acylation of these compounds in protonized form; compared to, for example, acetylation of alpha-methyldopamine (R. J. Borgman et al, "Alphamethyldopamine Derivatives, Synthesis and Pharmacology," J. Med. Chem., 17, 427–430, 1974) or acetylation of 3,4-dihydroxyphenylalanine (Bodor et al, "Improved Delivery Through Biological Membranes", 4. Prodrugs of L-DOPA" J. Med. Chem. 20, 1435–1445, 1977).

SUMMARY OF THE INVENTION 3,4-Di-isobutyryloxy-N-[3-(4-isobutyryloxyphenyl)-1-methyl-n-propyl]-beta-phenethylamine is a novel form of cardiac contractility agent that may be substituted for the known compound 3,4-dihydroxy-N-[3-(4-hydroxyphenyl)-1-methyl-n-propyl]-beta-phenethylamine in the intravenous method of Tuttle et al. The cyclodextrin form of 3,4-di-isobutyryloxy-N-[3-(4-isobutyryloxyphenyl)-1-methyl-n-propyl]-beta-phenethylamine may be substituted for the oral form of the aforementioned copending application.

In accordance with a second aspect of the invention there is provided a novel complex of 3,4-di-isobutyryloxy-N-[3-(4-isobutyryloxyphenyl)-1-methyl-n-propyl]-beta-phenethylamine with a cyclodextrin.

3,4-Di-isobutyryloxy-N-[3-(4-isobutyryloxyphenyl)-1-methyl-n-propyl]-beta-phenethylamine in its uncomplexed form may be substituted for 3,4-dihydroxy-N-[3-(4-hydroxyphenyl)-1-methyl-n-propyl]-beta-phenethylamine in the intravenous procedures of Tuttle et al. 3,4-Di-isobutyryloxy-N-[3-(4-isobutyryloxyphenyl)-1-methyl-n-propyl]-beta-phenethylamine in its cyclodextrin form, which may be the alpha, beta or gamma form but preferably the beta form, may be orally administered, e.g., as a tablet, in accordance with the method set forth in the aforementioned copending application, substituting an equimolar amount of the 3,4-di-isobutyryloxy-N-[3-(4-isobutyryloxyphenyl)-1-methyl-n-propyl]-beta-phenethylamine cyclodextrin complex herein for the 3,4-dihydroxy-N-[3-(4-hydroxyphenyl)-1-methyl-n-propyl]-beta-phenethylamine cyclodextrin complex of the aforementioned copending application.

With respect to the oral dosage unit form of the cyclodextrin complex of 3,4-di-isobutyryloxy-N-[3-(4-isobutyryloxyphenyl)-1-methyl-n-propyl]-beta-phenethylamine. As a pharmaceutically effective amount may be mentioned from about 10 to about 150 milligram per kilogram body weight per day for an oral dosage unit form, and still more preferably about 50 mg/kg/day. Dosage unit form for oral administration include the conventional dosage formulations for pharmaceuticals, with tablets being particularly suitable. Although excipients may generally be added to the active ingredient in the formulation of tablets, it is unnecessary to do so in the present invention. For examples, tablets of about 1.5 gram consisting entirely of the active complex may be manufactured through conventional tableting techniques, the patient taking several of these tablets at one time on a once a day basis in accordance with a preferred aspect of the present invention. Sublingual dosage forms are preferrably prepared in the form of a wafer and suppository forms are prepared by compounding the complex with a conventional wax.

The following examples further illustrate the invention:

EXAMPLE I 3,4-Dihydroxy-N-[3-(4-hydroxyphenyl)-1-methyl-n-propyl]-beta-phenethylamine hydrochloride (0.5 g, 1.4 mmol) was dissolved in trifluoroacetic acid (8 ml) at room temperature. To this solution isobutyryl chloride (0.47 g, 4.2 mmol) was added dropwise. The mixture was stirred for 15 minutes and volatiles evaporated in vacuo. To the oily residue isopropanol (0.5 ml) was added and again all volatiles were distilled off in vacuo. Upon standing the oily residue eventually crystallized. Recrystallization from ether-cyclohexane mixture yielded white crystals (0.58 g), M.P. 83°–86° C. Thin layer chromatography on silica gel using chloroform-acetone (1:1) as eluent indicated that product is not contaminated by starting material, but contains a minor contaminant with a lower mobility.

EXAMPLE II 3,4-Dihydroxy-N-[3-(4-hydroxyphenyl)-1-methyl-n-propyl]-beta-phenethylamine hydrochloride (1 g, 2.9 mmol) was dissolved in trifluoroacetic acid (15 ml) at 22° C. While stirring was continued isobutyryl chloride (0.96 g, 9 mmol) was added dropwise and the reaction left to proceed for 20 minutes. Thereafter volatiles were evaporated in vacuo, isopropanol (5 ml) was added again all volatiles were distilled off in vacuo. The oily residue, according to thin layer chromatography on silica gel with chloroform-methanol (5:1) elution, has in addition to the main product three minor contaminants, all of them of lower mobility. The oily residue was dissolved in boiling diethyl ether (30 ml) and cyclohexane (5 ml) was added and solution clarified by hot filtration with active carbon (Norit). Solution was thereafter left at 0° C. while white rhomboid crystals separated (1.49 g), M.P. 80°–82° C. Additional recrystallization from ethercyclohexane yielded crystals (1.19 g), M.P. 84°–86° C., in which only very minor contaminants could be detected. Thin layer chromatography was performed on silica gel with acetone for elution and ultraviolet light and iodine for detection; the triester had Rf 0.64–0.66, contaminants Rf 0.28 and 0.19. Elementary analysis indicated that the compound is a salt of 3,4-di-isobutyryloxy-N-[3-(4-isobutyryloxyphenyl)-1-methyl-n-propyl]-beta-phenethylamine with trifluoroacetic acid.

$C_{32}H_{42}NO_8F_3$: Calc.: C 61.43%; H 6.77%; N 2.24%; O 20.46%; F 9.11%; Found: C 61.44%; H 6.49%; N 2.28%; Cl 0.13%.

EXAMPLE III 3,4-Dihydroxy-N-[3-(4-hydroxyphenyl)-1-methyl-n-propyl]-beta-phenethylamine hydrochloride (1 g, 2.9 mmol), trifluoroacetic acid (15 ml), and isobutyryl chloride (1.26 g, 11.6 mmol) were reacted together for 15 minutes as described in Example I. The recrystallization performed as in Example I giving white crystals (1.2 g) of the same purity.

EXAMPLE IV 3,4-Dihydroxy-N-[3-(4-hydroxyphenyl)-1-methyl-n-propyl]-beta-phenethylamine hydrochloride (1 g, 2.9 mmol), trifluoroacetic acid (5.8 ml), and isobutyryl chloride (1.23 g, 11.6 mmol) were reacted together as described in Example I. The same purification yielded white crystals (0.89 g) with the same chromatographic characteristics.

In other experiments it was established that prolongation of reaction time to 2 hours or longer led to a decrease in quality of the product. Another anion other than trifluoroacetic acid can be used.

EXAMPLE V 2,6-Di-O-methyl-beta-cyclodextrin (1.6 g) was dissolved in water (2 ml) at 20° C. and 3,4-di-isobutyryloxy-N-[3-(4-isobutyryloxyphenyl)-1-methyl-n-propyl]-beta-phenethylamine (0.3 g) dissolved in ethanol (2 ml) was slowly added. After 3 hours standing at room temperature the solution was freeze dried yielding a white powder (1.86 g). Thin layer chromatography in the systems described above indicated that there was no hydrolysis of ester group during the preparation of the complex. Two independent samplings of the complex were made and were found to contain 14.85 and 15.00% of drug. The analysis was performed by spectrophotometry at 266 nm.

EXAMPLE VI 2,3,6-Tri-O-methyl-beta-cyclodextrin (1.67 g) was dissolved in water (8 ml) at 22° C. and to this solution was added a solution of 3,4-di-isobutyryloxy-N-[3-(4-isobutyryloxyphenyl)-1-methyl-n-propyl]-beta-phenethylamine (0.3 g) in ethanol (2 ml). The suspension was stirred for 3 hours at room temperature and then freeze dried, yielding a white powder (1.87 g) containing, in two independent samplings, 18.8 and 19.5% of the drug. Thin layer chromatograph was used to confirm that no hydrolysis of ester group occurred during the complexation.

EXAMPLE VII

An equimolar amount of an alpha or gamma cyclodextrin may be substituted for the beta-cyclodextrin of the preceding examples to make the corresponding alpha or gamma forms.

EXAMPLE VIII

Substituting an equimolar amount of 3,4-di-isobutyryloxy-N-[3-(4-isobutyryloxyphenyl)-1-methyl-n-propyl]-beta-phenethylamine 2,5-di-O-methyl-beta-cyclodextrin complex of Example VI for the 5 mg 3,4-dihydroxy-N-[3-(4-hydroxyphenyl)-1-methyl-n-propyl]-beta-phenethylamine beta-cyclodextrin in the aforementioned copending application, the complex may be administered to clinically instrumented mongrel dogs to measure pressure in the left vetnricle of the heart, to demonstrate the utility as an oral cardiac contractility agent.

What is claimed is:

1. A complex of 3,4-diisobutyryloxy-N-[3-(4-isobutyryloxyphenyl)-1-methyl-n-propyl]-beta-phenethylamine which is complexed with at least one mol of cyclodextrin per mol 3,4-di-isobutyryloxy-N-[3-(4-isobutyryloxyphenyl)-1-methyl-n-propyl]-beta-phenethylamine.

2. The complex of claim 1 wherein said cyclodextrin is a beta-cyclodextrin.

3. The complex of claim 2 wherein said cyclodextrin is 2,6-di-O-methyl-beta-cyclodextrin.

4. A complex of claim 1, 2 or 3 which is complexed with about two mol of cyclodextrin per mol 3,4-di-isobutyryloxy-N-[3-(4-isobutyryloxyphenyl)-1-methyl-n-propyl]-beta-phenethylamine.

* * * * *